(12) United States Patent
Welter et al.

(10) Patent No.: US 7,052,743 B2
(45) Date of Patent: May 30, 2006

(54) CHIRAL COMPOUNDS AND COMPOSITIONS CONTAINING THE SAME

(75) Inventors: Thomas R. Welter, Webster, NY (US); Krishnan Chari, Fairport, NY (US)

(73) Assignee: Eastman Kodak Company, Rochester, NY (US)

( * ) Notice: Subject to any disclaimer, the term of this patent is extended or adjusted under 35 U.S.C. 154(b) by 173 days.

(21) Appl. No.: 10/651,692

(22) Filed: Aug. 29, 2003

(65) Prior Publication Data

US 2005/0072961 A1   Apr. 7, 2005

(51) Int. Cl.
*C09K 19/58* (2006.01)
*C09K 19/52* (2006.01)
*C07C 69/76* (2006.01)

(52) U.S. Cl. ............... 428/1.1; 252/299.01; 252/299.2; 560/80; 560/256

(58) Field of Classification Search ................ 428/1.1; 252/299.01, 299.2, 299.5; 560/80, 256
See application file for complete search history.

(56) References Cited

U.S. PATENT DOCUMENTS

| 3,945,968 A | 3/1976 | Goletto |
| 4,346,167 A | 8/1982 | Imatomi et al. |
| 4,895,793 A | 1/1990 | Seto et al. |
| 5,053,555 A | 10/1991 | Yeager et al. |

FOREIGN PATENT DOCUMENTS

| EP | 0 307 951 | 3/1989 |
| JP | 9-244231 | 9/1997 |

OTHER PUBLICATIONS

Birman et al., "1,1'-Spirobilindane-7,7'-diol: a novel, C2-symmetry chiral ligand", Tetrahedron: Asymmetry, vol. 10, pp. 125-131, 1999.*
CAPLUS 1969: 114866.*
JP 9-244231—Abstract.
J. Am. Chem. Soc., vol. 105, No. 25, 1983, Gottarelli et al. "Induction of Cholesteric Mesophase".
Birman, Vladimir B. et al: "1,1'-Spirobiindan-7,7'-diol: a novel, C2-symmetric chiral ligand" Tetrahedron: Asymmetry, 10(1), 125-131 CODEN: TASYE3; ISSN: 0957-4166, 1999, XP002315481 P. 126, Scheme 1, e.g. compounds 14 to 16; p. 127, compounds 16 to 19; Scheme 2; p. 130, item 3.9.

Database Beilstein, Institut Zur Forderung Der Chemischen, Wissenschaften, Frankfurt am Main, DE; XP002315483, Database accession No. BRN 2034658, abstract & Blatchly et al.: "Thiele-Winter Acetoxylation of Quinones. Part IV. Quinones containing One or More t-Butyl Groups" J. Chem. Soc. Perkin Trans. 1, 1972, pp. 2286-2291, XP009043084.
Database CA Online, Chemical Abstracts Service, Columbus, Ohio, US; Tan, Shiro et al: "Novel diazonaphthoquinone photoactive compound for g-line/i-line compatible positive photoresist," XP002315484, retrieved from STN, Database assession No. 1990:601153, abstract, and Proceedings of SPIE—The International Society for Optical Engineering, 1262 (Adv. Resist Technol. Process. 7), 513-26 CODEN: PSISDG; ISSN: 0277-786X, 1990.
Database CA Online, Chemical Abstracts Service, Columbus, Ohio, US; Sanchez-Viesca, F. et al: "Preparation and spectroscopy study of 4,4', 6,6', 7,7'-hexamethoxy-3, 3, 3', 3'-tetramethyl-1, 1'-spiro-bis-hydrinden" XPOO2315484, retrieved from STN, Database accession No. 1981: 461829, abstract, and Revista Latinoamericana de Quimica, 12(1), 27-9 CODEN: RLAQA8: ISSN; 0370-5943, 1981.
Dtabase CA Online, Chemical Abstracts Service, Columbus, Ohio, US; Uenishi, Kazuya et al: "Structural effects of diazonaphthoquinonephotoactive compound backbone on resist lithographic properties," XP002315486, retrieved from STN, Database accession No. 1991:690953, abstract, and Proceedings of SPIE—The International Society for Optical Engineering, 1566 (Adv. Resist Technol. Process. 8), 102-16 CODEN: PSISDG; ISSN: 0277-786X, 1991.
Zhou, Hai et al: "Highly Enantioselective Copper-Catalyzed Conjugate Addition of Diethylzinc to Enones using Chiral Spiro Phosphoramidites as Ligands," Journal of Organic Chemistry, 68(4), 1582-1584 CODEN: JOCEAH; ISSN: 0022-3263, vol. 68, No. 4, 2003, pp. 1582-1584, XP002315482, p. 1582, Figure 1; sCHEME 1; Abstract.

* cited by examiner

Primary Examiner—Shean C. Wu
(74) Attorney, Agent, or Firm—Chris P. Konkol

(57) ABSTRACT

The invention relates to a novel class of compounds useful as chiral dopants, which compounds are available in both enantiomeric forms. Another aspect of the invention relates to such compounds having a enantiomeric excess of one enantiomeric form, which are useful in liquid crystal formulations. Such formulations are advantageous in displays and various other products.

18 Claims, No Drawings

CHIRAL COMPOUNDS AND COMPOSITIONS CONTAINING THE SAME

FIELD OF THE INVENTION

The present invention involves the formation of chiral nematic liquid crystal (LC) compositions using nematic materials in combination with chiral dopants.

BACKGROUND OF THE INVENTION

Chiral nematic, also known as cholesteric, liquid crystalline materials are useful in a variety of applications including various LC display components, reflective films, optical filters, polarizers, paints, and inks, among others. Methods for preparing such materials are well established. See, e.g., G. Gottarelli and G. Spada, *Mol. Cryst. Liq. Crys.*, 123, 377 (1985); G. Spada and G. Proni, *Enantiomer*, 3, 301 (1998). However, improvement is still needed. While early uses of chiral nematic compositions relied upon mixtures composed mostly of chiral components, more recently such materials are composed of nematic LC mixtures combined with small amounts of chiral dopants. In such new compositions the properties of the nematic host material, for example viscosity, birefringence, electrical anisotropy, and magnetic anisotropy among others, are tailored to the desired usage by altering the chemical composition of the nematic mixture, and then a chiral dopant is incorporated to induce helical twisting so as to provide the desired chiral nematic pitch. It is apparent that the properties of this chiral nematic composition are therefore a combination of the properties of the nematic host plus those of the dopant. It is further well understood that by reducing the amount of dopant, the properties of the host nematic LC formulation might be better preserved. Certainly, reducing the concentration of a specific dopant also increases the pitch of the resulting chiral nematic formulation. Many uses of chiral nematic compositions require the formulation to reflect or transmit visible light, thus requiring compositions with substantial helical twist, i.e. short helical pitch ("p"). These considerations indicate that dopants that induce large amounts of nematic helical twist per unit concentration are prized. The figure of merit for such materials is its Helical Twisting Power ("HTP" or $\beta$).

A dopant material's HTP ($\beta$) is defined, in a specified host at a particular temperature, by Eq (1):

$$\beta = (pcr)^{-1} \quad (1)$$

wherein the "p" is the measured helical pitch of the doped nematic ($\mu$m); "c" is measure of the dopant concentration (usually in terms of mole fraction, weight fraction, or weight percent on a unitless scale, wherein mole fraction and weight fraction is on a scale of 0 to 1); and "r" is the enantiomeric excess of the dopant (on a unitless scale of 0 to 1). Enantiomeric excess (r) is defined as the absolute value of the difference in mole fraction (F) of the two enantiomer in a sample r equals $|F_{(+)} - F_{(-)}|$. Thus, for a racemic mixture r equals $|0.5-0.5|=0$; for an enantiomerically pure material r equals $|1.0-0|=1$; and for a 75% pure mixture the r equals $|0.75-0.25|=0.5$. The larger the HTP the lower the concentration of dopant needed to provide a specific pitch, and thereby yield a particular reflectance or transmittance. The pitch of a chiral nematic formulation can be measured using a variety of optical techniques. For example, see Z. Dogic and S. Fraden, *Langmuir*, 16, 7820 (2000). The dopant concentration is as formulated and the enantiomeric excess can be measured via chiral high-performance liquid chromatography (HPLC) or nuclear magnetic resonance (NMR) spectroscopy. Typically, for useful enantiomerically pure dopants, their HTP's range from one to several hundred ($\mu$m$^{-1}$). Dopants with twisting power greater than 100 (based on dopant mole fraction) are often described as "high twist" dopants. The discovery of new dopants, particularly high twist dopants, is important to broadening the utility of chiral nematic formulations.

Not only can chiral nematic liquid crystals be formulated to reflect various wavelengths of incident electromagnetic radiation, but it is well understood that that reflected light is circularly polarized, depending upon the sense of chirality of the helical pitch. Thus, a chiral nematic displaying a right-handed helical mesostructure will reflect right-handed incident light. For many applications it is useful to be able to reflect both right-handed and left-handed senses of circularly polarized light, for example, in a vertically layered structure. It is further well known that enantiomers of a chiral-dopant structure induce the opposite polarity of helical rotation and, therefore, afford oppositely polarized light reflections. For this reason the preparation of enantiomeric pairs of dopants for use in separate light modulating layers can be particularly useful.

There are three general sources for obtaining substantially enantiomerically pure organic compounds for use as dopants or more likely as synthetic precursors for dopants: (1) compounds available from natural sources; (2) the preparative separation of racemic mixtures of enantiomers; or (3) chiral synthetic methods that directly afford desired enantiomers. Most commonly, only the latter two methods provide access to both enantiomers of a potential dopant. Natural sources generally provide only one of any enantiomeric pair, reflecting the fundamental chirality of life. Thus, using natural sources for dopants or their precursors can lead to limitations in dopant utility. A discovery of new dopants available from non-natural sources would therefore be especially useful.

SUMMARY OF THE INVENTION

Applicants have found a novel class of compounds useful as chiral dopants, which compounds are available in both enantiomeric forms. Another aspect of the invention relates to such compounds having a enantiomeric excess of one enantiomeric form. Yet another aspect of the invention relates to chiral nematic liquid crystal formulations comprising such chiral dopants. Such formulations are useful in displays and other products. Optionally the chiral dopants can be capable of polymerization.

DETAILED DESCRIPTION OF THE INVENTION

We have found that certain compounds represented by the following Structure 1 are useful as a source of chiral dopants. In particular, the enantiomerically enriched form of such compounds, including the substantially enantiomerically pure form, introduced into nematic compositions, afford useful chiral nematic mixtures.

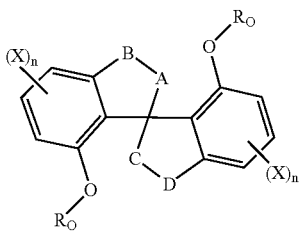

As evident, compounds of Structure 1 comprise a central nucleus comprising a spirodiphenoxy moiety. In Structure 1, A, B, C and D are independent divalent groups; each X is any independently selected ring substituent, n independently varies from 0 to 3, and the $R_O$ groups are independently selected from hydrogen or any substituent capping the phenolic oxygen in Structure 1. Preferably, A, B, C, and D are such that A and B comprise a first five or six-membered ring, and C and D comprise a second five or six-membered ring which rings share a spirocarbon atom to which A and C are attached.

A preferred embodiment is represented by the following Structure 2:

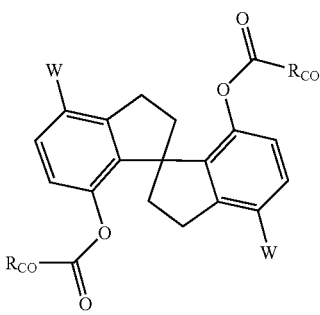

wherein W is hydrogen or a substituent and $R_{CO}$ is any suitable substituent.

In general, when reference in this application is made to a particular moiety or group it is to be understood that such reference encompasses that moiety whether unsubstituted or substituted with one or more substituents (up to the maximum possible number. For example, "alkyl" or "alkyl group" refers to substituted or unsubstituted alkyl, while "benzene group" refers to a substituted or unsubstituted benzene (with up to six substituents). Generally, unless otherwise specifically stated, substituent groups usable on molecules herein include any groups, whether substituted or unsubstituted, which do not destroy properties necessary for mesophase utility. Examples of substituents on any of the mentioned groups can include known substituents, such as: chloro, fluoro, bromo, iodo; hydroxy; alkoxy, particularly those "lower alkyl" (that is, with 1 to 12 carbon atoms, for example, methoxy, ethoxy; substituted or unsubstituted alkyl, particularly lower alkyl (for example, methyl, trifluoromethyl); thioalkyl (for example, methylthio or ethylthio), particularly either of those with 1 to 12 carbon atoms; substituted or unsubstituted alkenyl, preferably of 2 to 12 carbon atoms (for example, ethenyl, propenyl, or butenyl); substituted and unsubstituted aryl, particularly those having from 6 to 20 carbon atoms (for example, phenyl); and substituted or unsubstituted heteroaryl, particularly those having a 5 or 6-membered ring containing 1 to 3 heteroatoms selected from N, O, or S (for example, pyridyl, thienyl, furyl, pyrrolyl); acid or acid salt groups; such groups as hydroxyl, amino, alkylamino, cyano, nitro, carboxy, carboxylate, acyl, alkoxycarbonyl, aminocarbonyl, sulfonamido, sulfamoyl, sulfo, sulfonate, or alkylammonium; and other groups known in the art. Alkyl substituents may specifically include "lower alkyl" (that is, having 1–12 carbon atoms), for example, methyl, ethyl, and the like. Further, with regard to any alkyl group or alkylene group, it will be understood that these can be branched or unbranched and include ring structures.

A, B, C and D in Structure 1 can independently be any bivalent substituent such as methylene, oxygen, sulfur, sulfoxyl, sulfonyl, carbonyl, mono-substituted nitrogen (N—R), di-substituted carbon ($R_1$—C—$R_2$), wherein R, $R_1$ and $R_2$ are independently hydrogen or any substituent. It is preferred the A, B, C and D independently be methylene or di-substituted carbon ($R_1$—C—$R_2$). It is more preferred that either A or B (and/or C or D) be methylene with the other being either methylene or di-substituted carbon ($R_1$—C—$R_2$). It is most preferred that A and B (and/or C and D) are both methylene. In one embodiment, A and B are the same, respectively as C and D. R, R and R' can independently be the same as X. Organic carbon-containing substituents having 1 to 12 carbon atoms are preferred.

The X substituent in Structure 1 can be any substituent. It is preferred to be an oxygen-containing organic substituent and/or a carbon-containing substituent. Preferred oxygen-containing substituents include alkoxy, aryloxy, carboalkyl (O—C(=O)R), carboaryl (O—C(=O)Ar), carboalkoxy (O—C(=O)OR), carboaryloxy (O—C(=O)OAr) either substituted or unsubstituted. Preferred carbon-containing substituents include alkyl groups of about 1–20 carbons, cycloalkyl groups of about 1–20 carbons, aryl groups of about 6–20 carbons, alkaryl groups of about 6–20 carbons, and heterocyclic groups having at least one heteroatom and 2–20 carbons; all either substituted or unsubstituted. Other preferred oxygen-containing organic substituents include carboalkoxy (C—C(=O)OR), carboaryloxy (C—C(=O)OAr), aryl or alkyl ketones (C—C(=O)R) or (C—C(=O)Ar), all either substituted or unsubstituted. Other suitable X substituents include, but are not limited to halogens; cyano (—CN); hydroxyl, amino, alkylamino, cyano, nitro, carboxy, aminocarbonyl, sulfonamido, sulfamoyl, sulfo, sulfonate, or alkylammonium; as well as a siloxane residue or polymerizable groups as mentioned below.

Furthermore, any two members of the following set: X and $R_O$ on the same aromatic ring in Structure 1 may be joined to form a fused ring, either aliphatic, unsaturated or aromatic provided that creation of the ring will not interfere with the functioning of the chiral dopant.

The W group in Structure 2 can independently be hydrogen or any substituent as defined above for X. In one preferred embodiment, W is hydrogen.

In one preferred embodiment of Structure 1, both "n" subscripts are 0 (as in the case W is hydrogen in Structure 2) or 1 (as in the case when W is a substituent in Structure 2) as in Structure 2.

The $R_O$ group in Structure 1 is independently any substituent or hydrogen, preferably having 1 to 24 carbon atoms, more preferably 8 to 18 carbon atoms. It is preferred to be alkyl, cycloalkyl, aryl, aralkyl, carbonyl such as alkylcarbonyl, arylcarbonyl, alkoxycarbonyl, aryloxycarbonyl, alkylsulfoxy, or arylsulfonyl, substituted or unsubstituted. It is more preferred to be carbonyl, C(=O)R$_{CO}$, where R$_{CO}$ is aryl, alkyl, cycloalkyl, or alkaryl, or heterocyclic either substituted or unsubstituted. It is particularly preferred for the R$_{CO}$ group to contain an aromatic ring, for example, a phenyl-containing group. It is most preferred that R$_{CO}$ be aryl either substituted or unsubstituted as defined by: —R$_{CO}$=(Y-L)$_m$-Z: wherein L is a single bond e.g. —(Y)$_m$-Z or bivalent linking group chosen from the following groups: —C(=O)O—; —OC(=O)—; —CH$_2$CH$_2$—; —CH=CH—; —C≡C—; —OCH$_2$—; —CH$_2$O—; —N=CH—; —CH=N—; —OC(=O)O—; —C≡C—C≡C—; —COCH=CH—; —CH=CHCO—; —O—; —S—; -and SO$_2$; wherein Y and Z independently may be 1,4-phenylene in which, in addition, one or more methylene may be replaced by —N=, 1,4-cyclohexyl in which, in addition, one or more non-adjacent methylene units may be replaced by O or S, 1,4-cyclohexylene, 1,4-bicyclo[2.2.2]octylene, piperidine-1,4-diyl, naphthalene-1,6-diyl, dechydronaphthalene-1,6-diyl, 1,2,3,4-tetrahydronaphthalene-1,6-diyl, in which each of these groups be unsubstituted or mono-substituted or poly-substituted with halogen, cyano, isocyanato, or nitro groups; or alkyl, alkoxyl or alkanoyl groups bearing 1–12 carbons where one or more hydrogens may be substituted with chlorine or fluorine and wherein m=0, 1, 2, 3, 4. As indicated above, R$_O$ can form a fused ring with an X group. The two R$_O$ groups in Structure 1 (or the two RCO groups in Structure 2) can also be connected to form a bridge between the two phenyl rings in, respectively, the Structure 1 or Structure 2.

A few examples of compounds according to the present invention, which examples are merely illustrative and not intended to be limiting, are as follows:

I-1
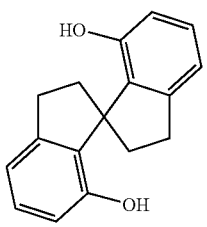

I-2
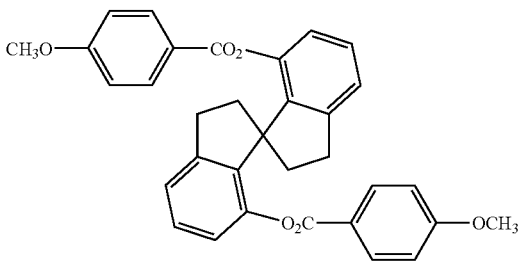

I-3
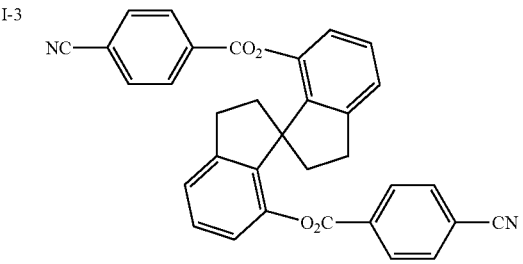

I-4
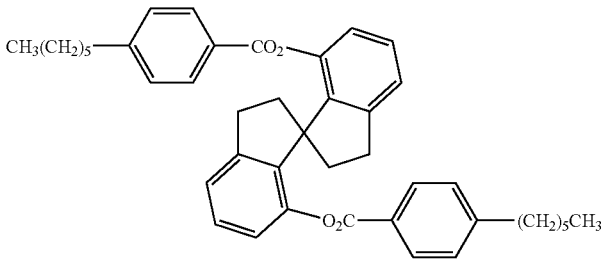

I-5
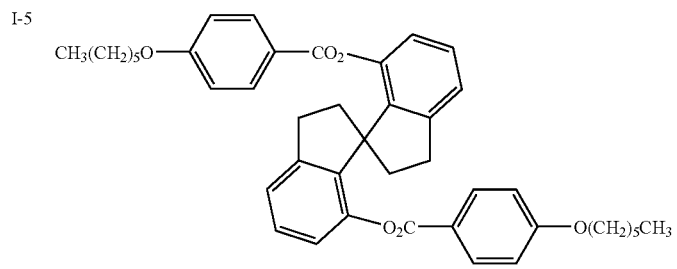
I-6
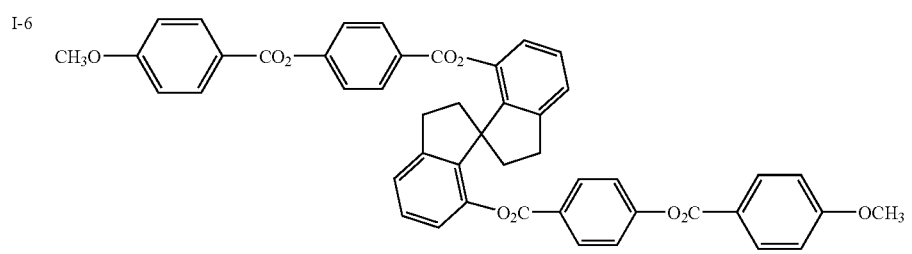
I-7
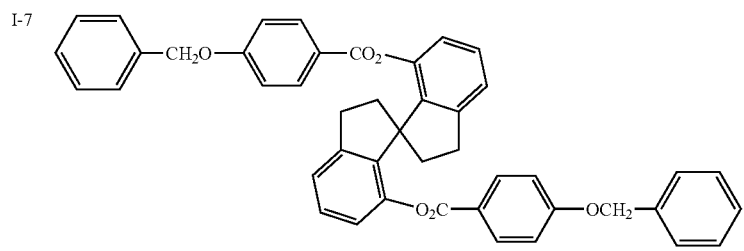
I-8
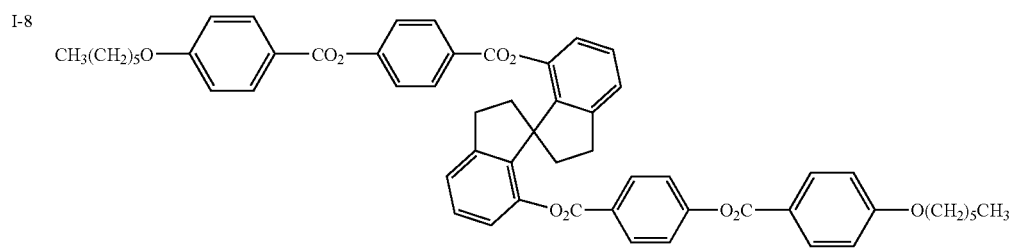
I-9
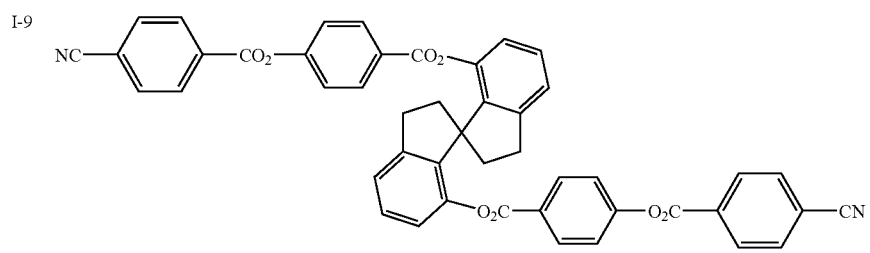
I-10
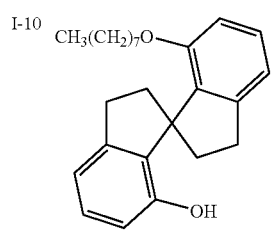

-continued
I-11
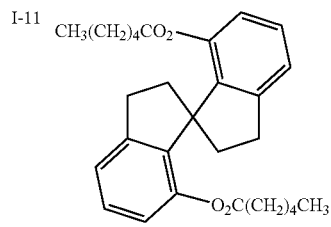
I-12
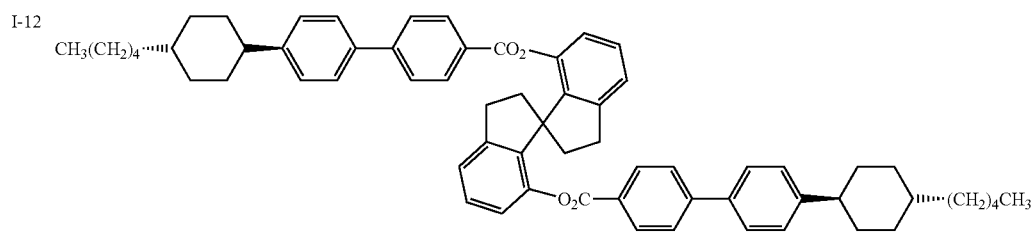
I-13
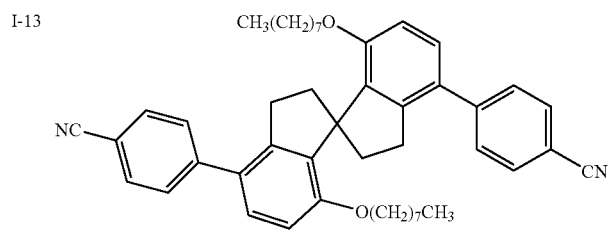
I-14
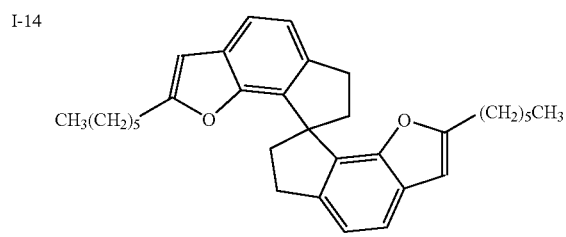
I-15
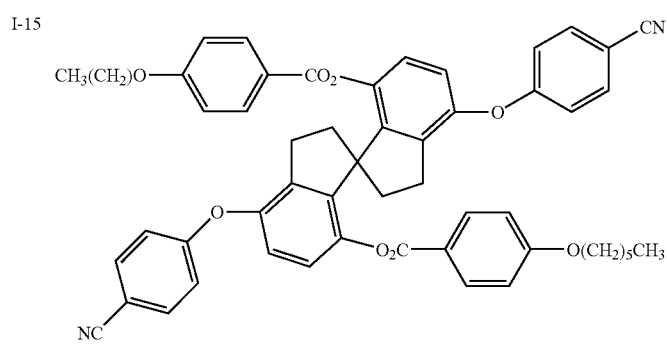
I-16
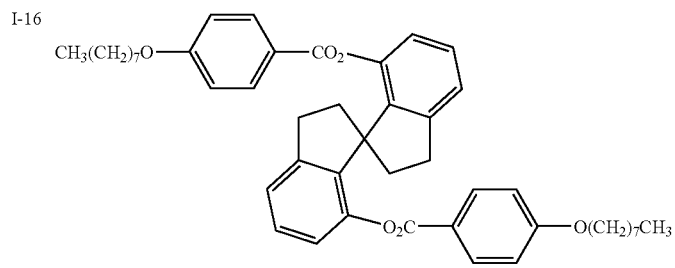

-continued
I-17
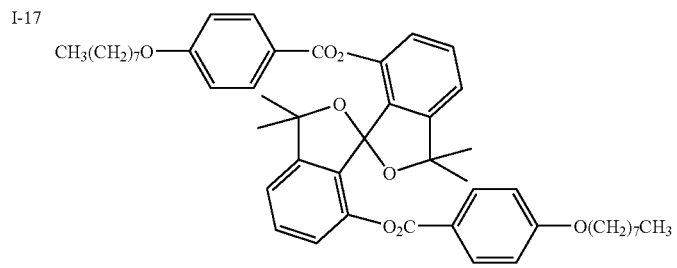
I-18
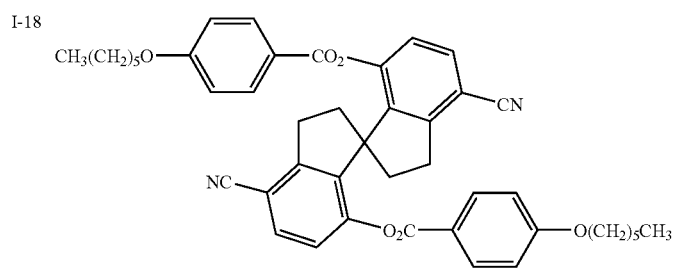
I-19
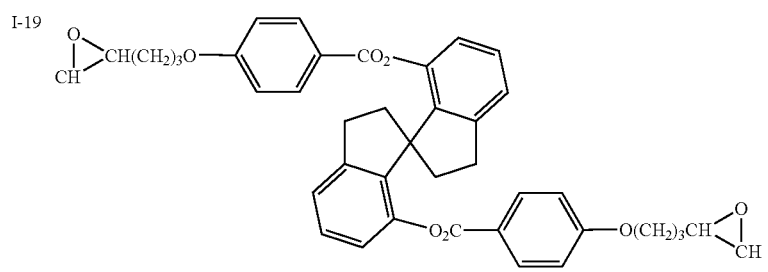
I-20
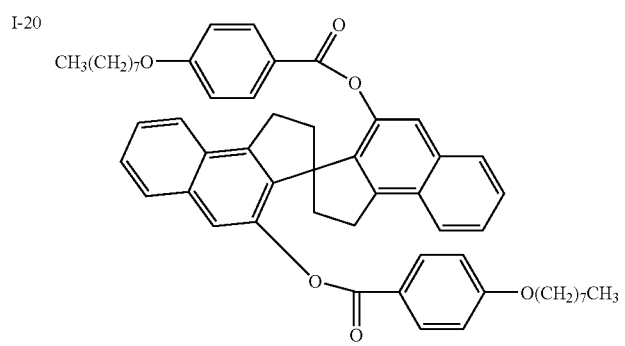
I-21
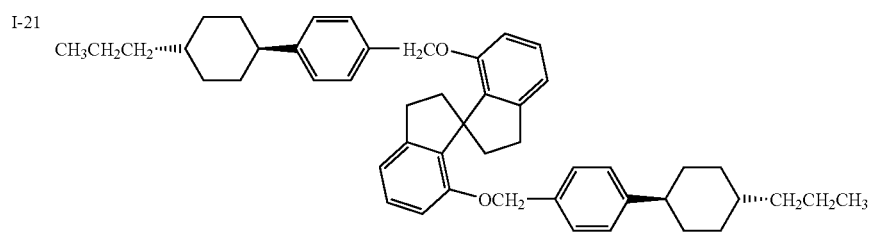

-continued
I-22
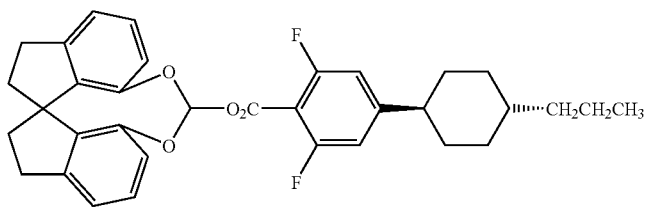
I-23
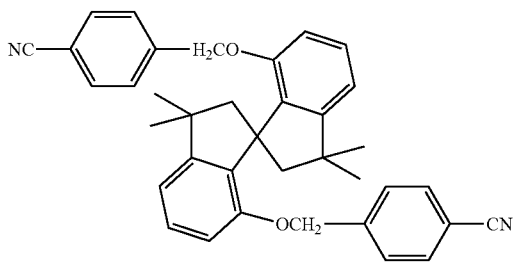
I-24
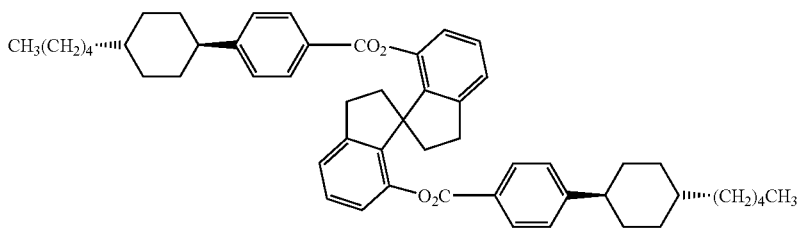
I-25
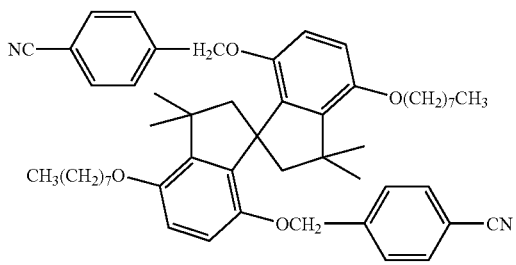
I-26
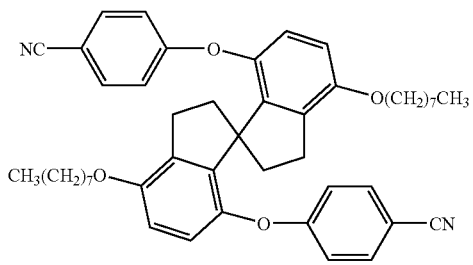
I-27
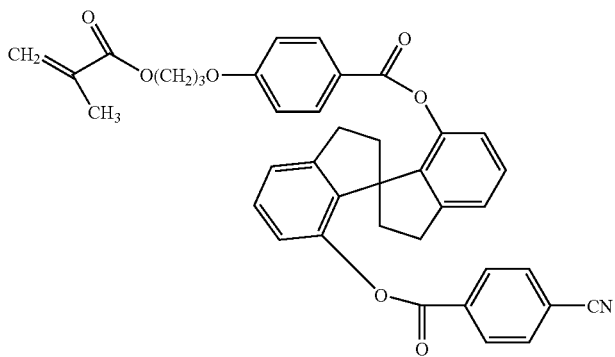

I-28
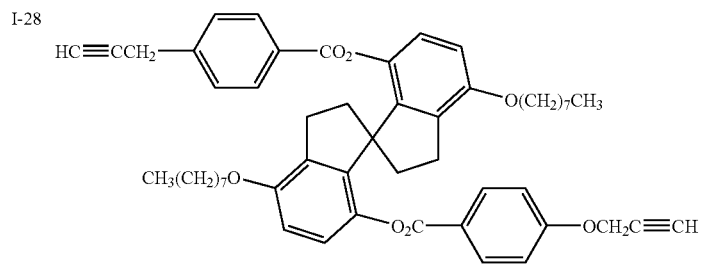
I-29
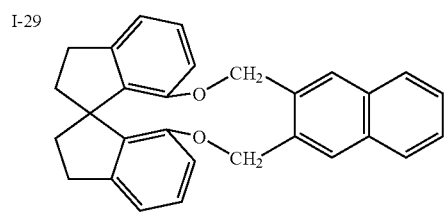
I-30
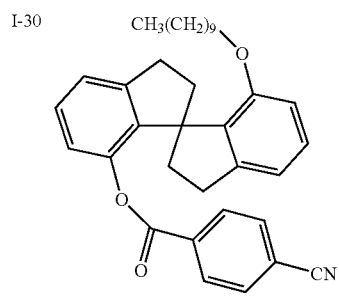
I-31
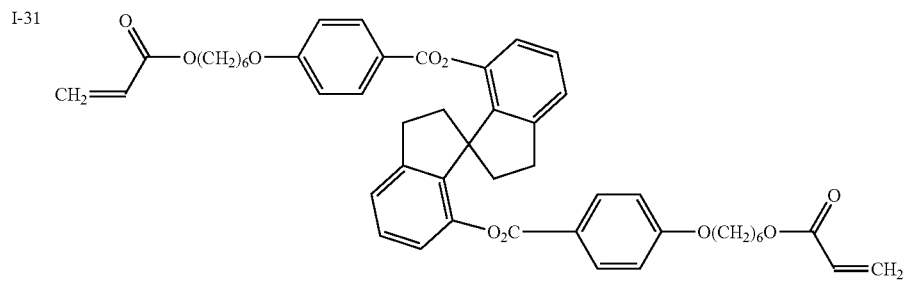
I-32
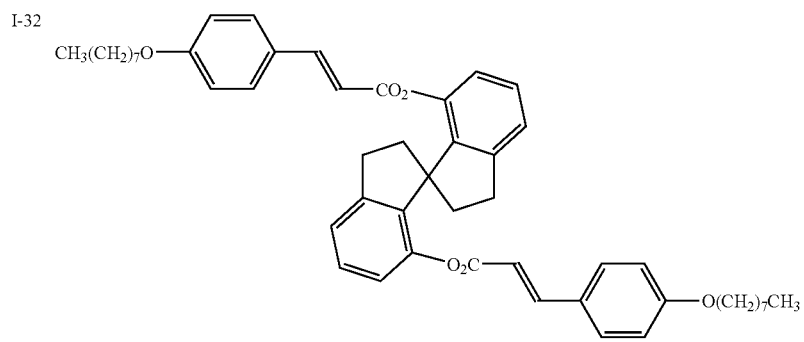

-continued

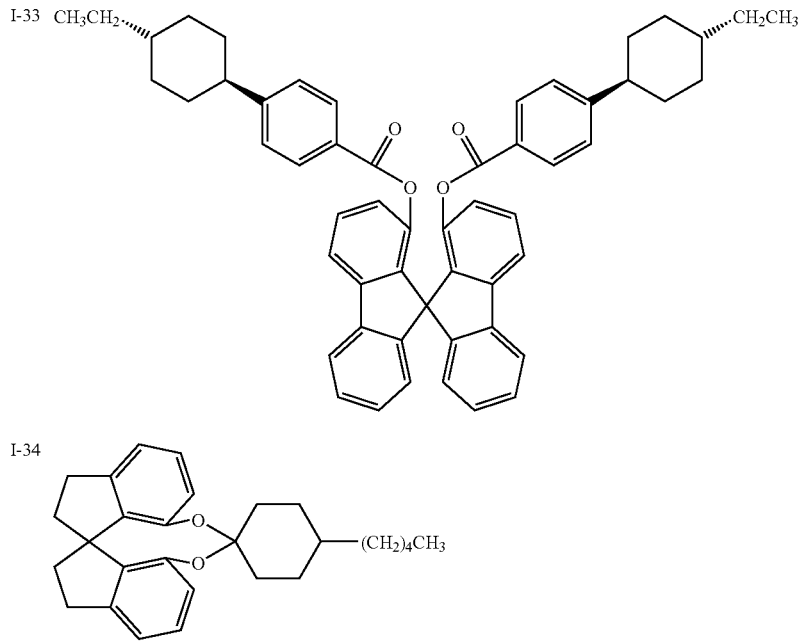

In a further embodiment, the dopant compound of Structure 1 or Structure 2 may contain as a part of A, B, C, D, X, $R_O$, $R_{CO}$, R, $R_1$, $R_2$, Y, and/or Z a polymerizable group, including, for example, a vinyl, acryloyl, methacryloyl, styryl, cyanoacrylate, vinyl ether, vinyl ester, isocyanate, epoxy, and/or derivatives thereof that are polymerizable moieties or a siloxane residue.

In one preferred embodiment of Structure 1, A is a carbon atom bearing two groups $R_A$, $(C(R_A)_2)$, B is a carbon atom bearing two groups $R_B$ $(C(R_B)_2)$, C is a carbon atom bearing two groups $R_C$, $(C(R_C)_2)$, and D is a carbon atom bearing two groups $R_D$, $(C(R_D)_2)$, wherein each $R_A$, $R_B$, $R_C$, and $R_D$ group is independently hydrogen or a substituent such as X above, preferably hydrogen or an organic substituent such as a substituted or unsubstituted alkyl; and X is any independently selected substituent, n varies from 0–3, and $R_O$ is a suitable substituent. In a preferred embodiment, the $R_O$ groups in Structure 1 are independently $R_{CO}$ as in Structure 2.

In a more preferred embodiment of Structure 1, the A, B, C and D groups are each methylene (—$CH_2$—) as in Structure 2; each X is any independently selected substituent, n varies from 0–3, and each $R_O$ is independently a suitable substituent.

In another more preferred embodiment of Structure 1, the A, B, C and D groups are each methylene, each X is independently H or a substituent; and n is 1 on both rings common to the spirocarbon with the proviso that any X substituent in each ring is found on the carbon para (C-4 and C-4') to the indicated oxygen substituent, as in Structure 2, and each $R_O$ is any suitable substituent.

An example of a particularly preferred embodiment is described by Structure 2 wherein X is replaced by hydrogen and $R_{CO}$ is a carbocyclic aromatic substituent either substituted or unsubstituted.

Compounds of the present invention, used in a non-racemic mixture or with an enantiomeric excess of one enantiomer, are useful as chiral dopants in liquid crystal compositions in an effective amount. One or more chiral dopants can be used cumulatively in an effective amount, either of Structure 1 or combined with other types of dopants. Suitably, the compound of Structure 1 can be used in the amount of 0.1 to 20 weight percent, based on the total weight of the liquid crystal composition, preferably 0.5 to 10 weight percent, more preferably 1 to 6 weight percent. Preferably the non-racemic mixture comprises at least 60 weight percent of one of the enantiomers, based on the weight of both enantiomers, preferably at least 80 weight percent, more preferably greater than 90 weight percent [may want to include corresponding r values]. The enantiomeric excess is greater than 0, preferably greater than 0.6. Most preferably the non-racemic mixture is a substantially or essentially pure enantiomer. As mentioned above, the more pure the enantiomer, the less chiral dopant necessary to obtain the desired HTP and, hence, less chance of incompatibilities or adversely affecting the desired anisotropic properties of the liquid crystal composition.

Preferably the HTP, on a dopant mole fraction basis, of the compound of Structure 1, when used in a particular liquid crystal composition, is greater than 80, more preferably at least 100, most preferably greater than 100.

Compounds of this invention can be readily prepared by those skilled in the art employing standard chemical transformations. Further these materials can be isolated in enantiomerically pure using standard methods including but not limited to: chiral HPLC, chiral synthesis, chemical or chromatographic separation of chiral derivatives of the spirophenol, e.g. via diastereomeric esters, urethanes, carbonates, and the like.

The preparation of the spirophenol derivative of the following substructure 3, wherein W' is hydrogen or selected substituents, has been previously described.

3

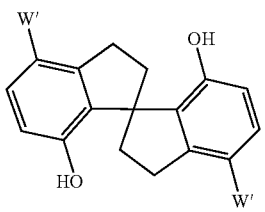

See S. Tan et al., Japanese Kokai (1994) JP 06308722 A2; Y. Kawabe et al., Japanese Kokai (1992) JP 04296755 A2; and T. Tanaka, M. Miyaguchi, R. Mochisuki, S. Tanaka, M. Okamoto, Y. Kitajima, and T. Miyazaki, *Heterocycles*, 25(1), 463–84(1987). See also V. Birman, A. Rheingold, and K-C. Lam, *Tetrahedron: Asymmetry*, 10(1), 125–131(1999). The preparative isolation of the enantiomerically pure derivatives has also been described. See, for example, J-H. Zhang, J. Liao, X. Cui, K-B. Yu, J. Zhu, J. G. Deng, S. F. Zhu, L. X. Wang, O. L. Zhou, L. W. Chung, and T. Ye, *Tetrahedron: Asymmetry*, 13(13), 1363–1366(2002). These and related methods may be employed to prepare enantiomerically enriched samples of the requisite spirophenols.

The use of chiral compounds of the present invention, or a polymerized form thereof, in admixture with a liquid crystal material, can be used for a wide variety of uses, including displays, polarizers, color filters, non-absorptive color filters, liquid crystal pigments for decorative or security purposes or coatings, optical switching, and optical information storage. For example, compositions according to the present invention can be used for making interference pigments with a viewing-angle-dependent color impression in printing inks and surface coatings. The compounds of the present invention can also be used in diagnostic, medical, or cosmetic compositions. For example, liquid crystal compositions in accordance with the present invention can be used to detect body temperature or to protect the human skin or hair from UV radiation.

The liquid crystalline composition can comprise STN, TN, chiral nematic, and ferroelectric materials or compounds. Preferably, the material comprises one or more liquid crystal compounds forming a chiral nematic material. The composition can be coated on a substrate, for example, during the manufacture of a display comprising the coated substrate. In one embodiment of a display, the liquid crystalline composition is disposed between first and second electrodes, wherein the chiral compound according to the present invention is a chiral dopant in liquid crystals.

Novel liquid crystalline compositions contain one or more chiral compounds of the Structure 1 or 2 as chiral dopants, usually in concentrations of from 0.1 to 10% by weight, based on the total amount of the liquid crystal. The concentration can be selected so that the desired interference hue is formed. Higher concentrations shift the hue into the blue region, and lower ones shift it into the red region.

Preferably, the liquid crystal mixture comprises 2 to 25 compounds, preferably 3 to 15 compounds. Particularly suitable liquid crystalline compositions are those in which the achiral liquid crystalline compounds comprise cyclic compounds, for example biphenyls, as will be appreciated by the skilled artisan. Suitable liquid crystalline compounds are well known to the skilled artisan. The liquid crystalline compositions can advantageously be used for coating substrates. Examples of suitable substrates are metal surfaces, plastic surfaces, glass or ceramic surfaces or films. Furthermore, the novel liquid crystalline compositions can be used for the preparation of liquid crystal displays. To this end, the compositions are, for example, applied to a substrate, preferably a polymeric film, if desired by knife coating or other physical influences. One embodiment of a display in which domains of a cholesteric liquid crystal composition are dispersed in a polymeric matrix, disposed between electrodes is, for example, disclosed in U.S. Pat. No. 6,236,442 to Stephenson et al. and U.S. Pat. No. 5,695,682 issued Dec. 9, 1997 to Doane et al., the disclosures of which are incorporated by reference. In one embodiment, a display comprises: (a) a flexible transparent support; (b) a patterned first conductor layer comprising transparent first conductors; (c) a patterned second conductor layer comprising second optionally transparent conductors; and (d) at least one imaging layer comprising domains of polymer-dispersed chiral nematic (cholesteric) liquid crystal material dispersed in a continuous polymeric matrix, the imaging layer disposed between the first and second conductors. Such chiral nematic liquid crystal material can exhibit two contrasting stable states, a reflecting planar state and a light-transmissive focal conic state, which two states can be switched from one to the other by application of suitable voltages.

EXAMPLES

1. Preparation of Compounds of the Invention:

The synthesis of representative compounds of the invention, as shown in Scheme 1 below, begins with preparation of racemic (R/S)-I-1, followed by chiral resolution of this enantiomeric mixture, and finally derivatization of the enantiomerically enriched spirodiphenols (R)-I-1 and (S)-I-1. The preparation of 1,1'-spirobiindan-7,7'-diol using a minor variant of the method described by Birman, et al., (vide supra). This synthetic route is outlined in Scheme 1.

Scheme 1

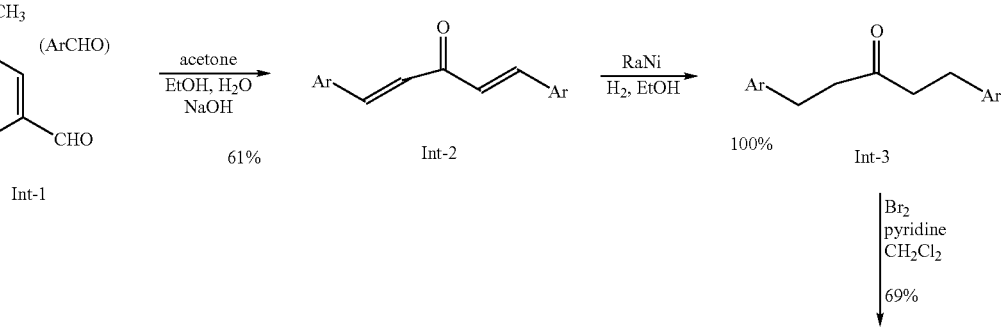

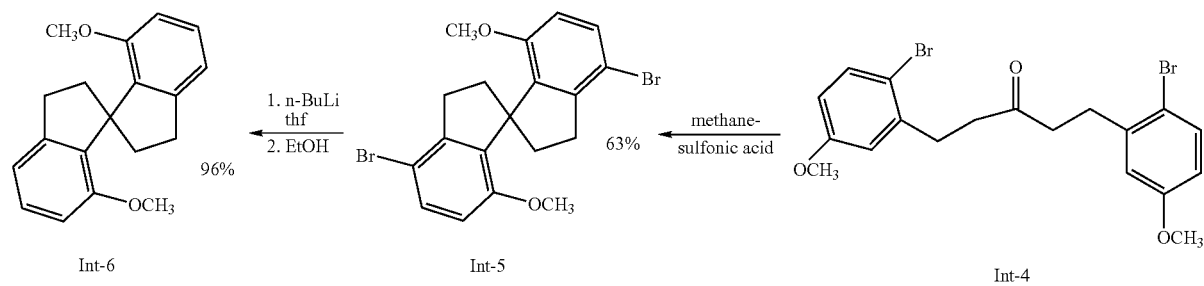

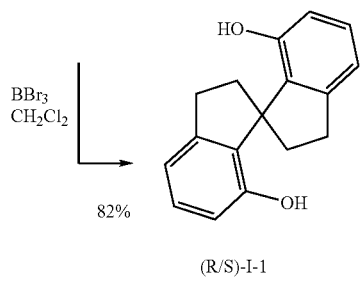

Again using the procedures of Birman, et al., the racemic (R/S)-I-1 was resolved via intermediary preparation and separation of menthyl carbonate esters, according to Scheme 2 below. Then finally, the thus prepared enantiomerically enriched spirodiphenol were derivatized using standard synthetic procedures, e.g., esterifications, alkylations, arylations, sulfonations, ketalization, acetalization, and the like. Included is a detailed, representative esterification procedure Scheme 3, shown below after Scheme 2.

Scheme 2

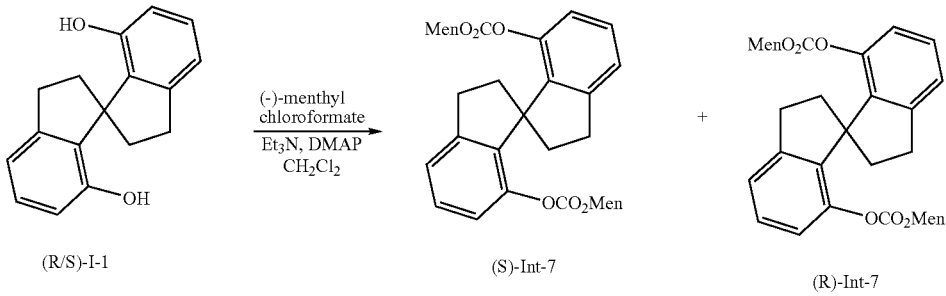

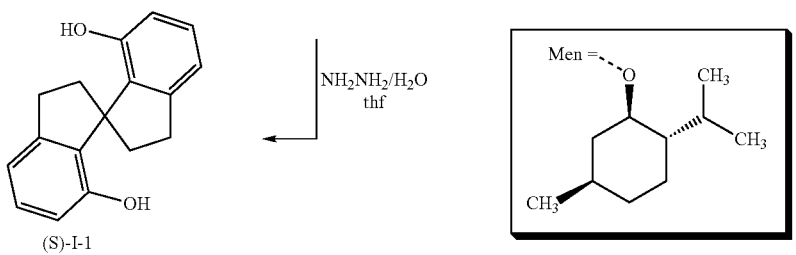

Scheme 3.

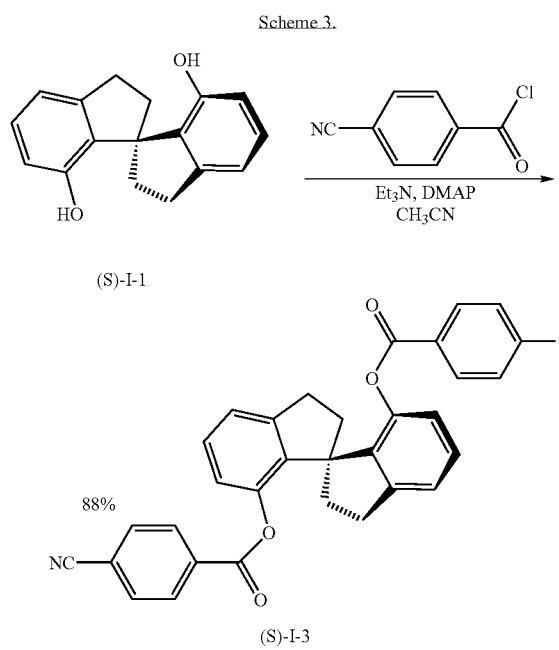

Preparation of (S)-I-3:

A solution of (S)-I-1 (0.63 g, 2.5 mmol; CAS 223259-63-0), 4-cyanobenzoyl chloride (0.96 g, 5.8 mmol; Int-8; CAS 6068-72-0) in 10 mL of acetonitrile was treated sequentially with 4-dimethylaminopyridine (0.1 g, DMAP; CAS 1122-58-3) and triethylamine (1 mL; CAS 121-44-8); a mildly exothermic reaction ensued with precipitate formation. After stirring at ambient temperature for 45 min the mixture was partitioned between dilute hydrochloric acid and ethyl acetate. The organics were washed with dilute aqueous sodium bicarbonate, dried, and concentrated in vacuo to provide a glassy residue. This material was chromatographed on silica gel, eluting with methylene chloride to provide a purified glassy residue. This residue was triturated with 25 mL of refluxing isopropyl ether, which upon chilling and filtration, afforded (S)-I-3 as a colorless solid, 1.13 g (88%). This material proved chromatically homogenous and displayed spectral characteristics consistent with its assigned structure.

Other compounds of the invention can be prepared via modifications of this procedure or via implementation of reactions known to those skilled in the art.

The following examples are presented to illustrate the practice of this invention, but are not meant to limit it in any way. All percentages are by weight unless otherwise indicated.

Example 1

Several enantiomerically pure derivatives of the invention were prepared (vide supra) and known amounts of these compounds combined with the commercially available liquid crystalline compound 4-n-pentyl-4'-cyanobiphenyl, 5CB, having the following structure:

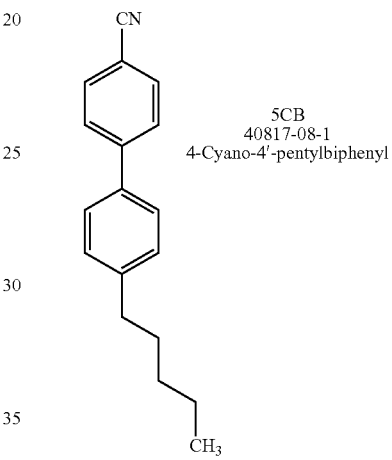

5CB
40817-08-1
4-Cyano-4'-pentylbiphenyl

The mixture was heated above its clearing point, thoroughly mixed and allowed to cool to ambient temperature. The pitches of these samples were then measured either from standard reflectance response curves or by the method of Dogic and Fraden (vide supra). The HTP's (β) of these samples, on a mole fraction basis, were then calculated as described above. Results of this experiment are found in Table 1 showing the HTP's in 5CB at ambient temperatures.

TABLE 1

| Compound | $R_7/R_{7'}$* | β (μm)$^{-1}$ |
|---|---|---|
| I-2 | —O$_2$C—⟨C$_6$H$_4$⟩—OCH$_3$ | 153 |
| I-3 | —O$_2$C—⟨C$_6$H$_4$⟩—CN | 153 |

TABLE 1-continued

[Structure: spirobiindane with R7 and R7' substituents]

| Compound | R7/R7'* | β (μm)⁻¹ |
|---|---|---|
| I-4 | —CO—C₆H₄—(CH₂)₅CH₃ | 170 |
| I-5 | —CO—C₆H₄—O(CH₂)₅CH₃ | 200 |
| I-6 | —O₂C—C₆H₄—O₂C—C₆H₄—OCH₃ | 238 |
| I-7 | —O₂C—C₆H₄—OCH₂—C₆H₅ | 200 |
| I-8 | —O₂C—C₆H₄—O₂C—C₆H₄—O(CH₂)₅CH₃ | 295 |

*Unless otherwise indicated $R_7$ and $R_{7'}$ are the same substituent.

Example 2

Several enantiomerically pure derivatives of the invention were prepared (vide supra) and known amounts of these compounds combined with the commercially available liquid crystalline mixture BL087 (described as a mixture of 5CB (25–40%), the structurally related 2CB wherein the n-pentyl group is replaced by an ethyl group (10–25%), and a proprietary LC mixture (35–65%)) available from Merck KGaA, Darmstadt, Germany. The mixture was heated above its clearing point, thoroughly mixed and allowed to cool to ambient temperature. The pitches of these samples were then measured either from standard reflectance response curves or by the method of Dogic and Fraden (vide supra). The HTP ($\beta$) of these samples was then calculated as described above, except on a weight percent basis. Results of this experiment are found in Table 2 below showing HTP's in 5CB at ambient temperatures.

TABLE 2

[Structure: spirobiindane with R7 and R7' substituents]

| Compound | R7/R7'* | β (μm)⁻¹ (wt. %)⁻¹ |
|---|---|---|
| I-1 | —OH | 0.03 |
| I-2 | —O₂C—C₆H₄—OCH₃ | 0.72 |

TABLE 2-continued
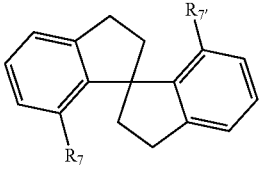
| Compound | R₇/R₇'* | $\beta$ $(\mu m)^{-1}$ (wt. %)$^{-1}$ |
|---|---|---|
| I-3 | 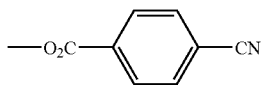 —O₂C—⟨C₆H₄⟩—CN | 0.72 |
| I-4 |  —CO—⟨C₆H₄⟩—(CH₂)₅CH₃ | 0.59 |
| I-5 | 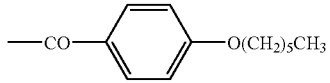 —CO—⟨C₆H₄⟩—O(CH₂)₅CH₃ | 0.75 |
| I-6 | 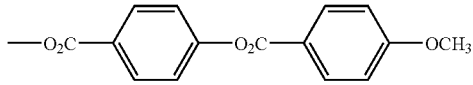 —O₂C—⟨C₆H₄⟩—O₂C—⟨C₆H₄⟩—OCH₃ | 0.75 |
| I-7 | 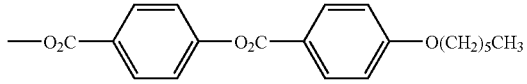 —O₂C—⟨C₆H₄⟩—O₂C—⟨C₆H₄⟩—O(CH₂)₅CH₃ | 0.84 |
| I-8 | 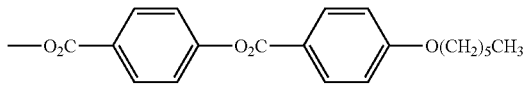 —O₂C—⟨C₆H₄⟩—O₂C—⟨C₆H₄⟩—O(CH₂)₅CH₃ | 0.61 |
| I-9 | 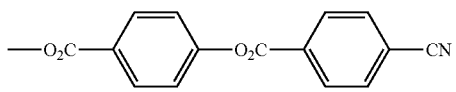 —O₂C—⟨C₆H₄⟩—O₂C—⟨C₆H₄⟩—CN | 0.67 |
| I-10 | —OH / —O(CH₂)₇CH₃ | 0.10 |
| I-11 | —O₂C(CH₂)₄CH₃ | 0.37 |
*Unless otherwise indicated R₇ and R₇' are the same substituent.

Example 3

Several enantiomerically pure derivatives of the invention were prepared (vide supra) and known amounts of these compounds combined with the commercially available liquid crystalline compound MBBA having the following structure:

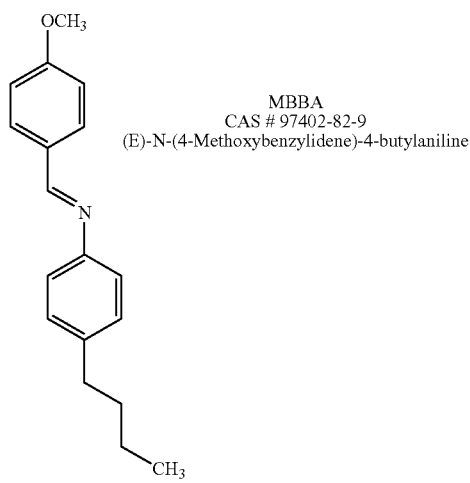

MBBA
CAS # 97402-82-9
(E)-N-(4-Methoxybenzylidene)-4-butylaniline

The mixture was heated above its clearing point, thoroughly mixed and allowed to cool to ambient temperature. The pitches of these samples were then measured either from standard reflectance response curves or by the method of Dogic and Fraden (vide supra). The HTP ($\beta$) of these samples was then calculated, on a mole fraction basis, as described above. Results of this experiment are found in Table 3 below showing HTP's in MBBA at ambient temperatures.

The invention has been described in detail with particular reference to certain preferred embodiments thereof, but it will be understood that variations and modifications can be effected within the spirit and scope of the invention

What is claimed is:

1. A chiral compound represented by the following structure:

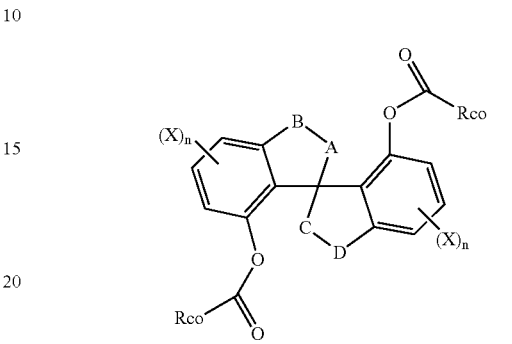

wherein A, B, C and D are the same and are selected from the group consisting of methylene, carbonyl, mono-substituted nitrogen (N—R), and di-substituted carbon ($R_1$—C—$R_2$), wherein R, $R_1$ and $R_2$ are independently hydrogen or a substituent and any two R, $R_1$ and $R_2$ groups on the same ring in said structure can optionally form a fused ring, the X groups are independently selected substituents, the n subscripts are independently 0, 1, 2, or 3, and the $R_{CO}$ groups are independently aryl, alkyl, cycloalkyl, alkaryl or heterocyclic, all either substituted or unsubstituted, and wherein any two X and/or $R_{CO}$ groups can optionally form a fused ring and the two $R_{CO}$ groups can optionally connect to form a bridge.

TABLE 3

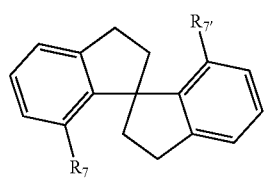

| Compound | $R_7/R_{7'}$* | $\beta$ ($\mu m$)$^{-1}$ |
|---|---|---|
| I-5 | —CO—⟨C6H4⟩—O(CH$_2$)$_5$CH$_3$ | 156 |
| I-6 | —O$_2$C—⟨C6H4⟩—O$_2$C—⟨C6H4⟩—OCH$_3$ | 237 |
| I-7 | —O$_2$C—⟨C6H4⟩—O$_2$C—⟨C6H4⟩—O(CH$_2$)$_5$CH$_3$ | 155 |
| I-8 | —O$_2$C—⟨C6H4⟩—O$_2$C—⟨C6H4⟩—CN | 238 |

*Unless otherwise indicated $R_7$ and $R_{7'}$ are the same substituent.

2. The compound of claim 1 wherein A, B, C and D are methylene or di-substituted carbon (R₁—C—R₂).

3. The compound of claim 1 wherein each X substituent is independently selected from the group consisting of oxygen-containing organic substituents and/or a carbon-containing substituents.

4. The compound of claim 3 wherein each X is independently selected from the group consisting of alkoxy, aryloxy, carboalkyl (O—C(=O)R), carboaryl (O—C(=O)Ar, in which Ar is an aryl group), carboalkoxy (O—C(=O)OR), carboaryloxy (O—C(=O)OAr, in which Ar is an aryl group), alkyl groups of about 1–20 carbons, cycloalkyl groups of about 1–20 carbons, aryl groups of about 6–20 carbons, alkaryl groups of about 6–20 carbons, carboalkoxy (C—C(=O)OR), carboaryloxy (C—C(=O)OAr, in which Ar is an aryl group), aryl or alkyl ketones (C—C(=O)R) or (C—C(=O)Ar, in which Ar is an aryl group), all either substituted or unsubstituted, or any two members of the X and R_{CO} groups on a ring may be joined to form a fused ring.

5. The compound of claim 1 having the following structure

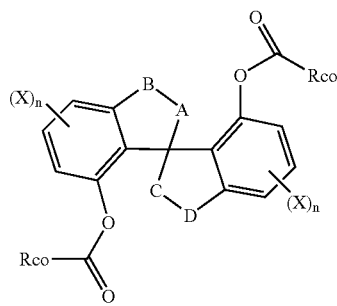

wherein each X is an independently selected substituent; each n is independently 0 to 3; and R_{CO} is as defined above.

6. The compound of claim 1 represented by the following structure:

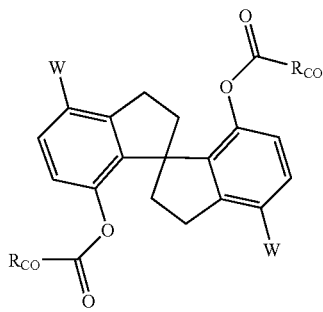

wherein W is a substituent or replaced by hydrogen and each R_{CO} is as defined above.

7. The compound of claim 6 wherein R_{CO} is a substituted or unsubstituted aryl.

8. The compound of claim 1 wherein the compound is capable of polymerization.

9. A material composition comprising an enantiomerically excess of one enantiomer of the compound of claim 1.

10. A liquid crystalline composition comprising as a chiral dopant admixed with a liquid crystal material, an effective amount of one or more chiral compounds, or a polymerized form thereof, represented by the following structure:

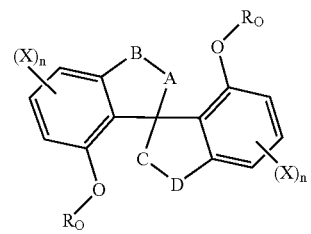

wherein A, B, C and D are independently selected from the group consisting of methylene, oxygen, carbonyl, mono-substituted nitrogen (N—R), and di-substituted carbon (R₁—C—R₂), wherein R, R₁ and R₂ are independently hydrogen or a substituent and any two R, R₁ and R₂ groups on the same ring in said structure can optionally form a fused ring, the X groups are independently selected substituents, the n subscripts are independently 0, 1, 2, or 3, and the R_O groups are independently a substituent capping each oxygen, and wherein any two X and/or R_O groups can optionally form a fused ring and the two R_O groups can optionally connect to form a bridge.

11. The liquid crystalline composition of claim 10 further comprising a polymer binder in which domains of the liquid crystal are dispersed.

12. The liquid crystalline composition of claim 10 wherein the liquid crystalline composition is STN, TN, chiral nematic, or ferroelectric.

13. The liquid crystalline composition of claim 10 wherein the liquid crystalline composition is chiral nematic.

14. A coated substrate comprising the liquid crystalline composition of claim 10.

15. A display comprising the liquid crystalline composition of claim 10 wherein the composition is disposed between first and second electrodes.

16. The display of claim 15 wherein the liquid crystalline composition is bistable and dispersed in the form of domains in a polymeric matrix.

17. A method of using an effective amount of a chiral compound of the structure of claim 9, or a polymerized form thereof, as a chiral dopant in liquid crystals comprising admixing the chiral compound with a liquid crystal material to obtain a liquid crystalline composition and using the composition in a display, polarizer, color filter, non-absorptive color filter, liquid crystal pigment for decorative coatings or security markings, optical switch, optical information storage, or a diagnostic or medical composition.

18. The method of claim 17 wherein the liquid crystalline composition is used in a display in which the liquid crystalline composition is disposed between first and second electrodes in the display.

* * * * *